(12) United States Patent
Brumbach

(10) Patent No.: US 6,582,440 B1
(45) Date of Patent: *Jun. 24, 2003

(54) NON-CLOGGING CATHETER FOR LITHOTRITY

(75) Inventor: Joseph F. Brumbach, Niles, IL (US)

(73) Assignee: Misonix Incorporated, Farmingdale, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 712 days.

(21) Appl. No.: 08/772,878

(22) Filed: Dec. 26, 1996

(51) Int. Cl.$^7$ ................................................ A61B 17/22
(52) U.S. Cl. .................. 606/128; 606/127; 606/169; 604/22
(58) Field of Search ................. 606/1, 127, 107, 606/128, 167, 169, 171, 185; 604/19, 22, 35, 118, 187, 537, 319, 902, 128, 540, 542; 601/12, 6

(56) References Cited

U.S. PATENT DOCUMENTS

| | | | |
|---|---|---|---|
| 3,785,382 A | * | 1/1974 | Kloiber et al. ............... 606/128 |
| 4,660,573 A | | 4/1987 | Brumbach |
| 4,942,878 A | | 7/1990 | Dory |
| 4,962,755 A | | 10/1990 | King et al. |
| 5,080,101 A | | 1/1992 | Dory |
| 5,143,073 A | | 9/1992 | Dory |
| 5,158,070 A | | 10/1992 | Dory |
| 5,254,121 A | | 10/1993 | Manevitz et al. |
| 5,354,265 A | * | 10/1994 | Mackool ..................... 606/128 |
| 5,425,735 A | | 6/1995 | Rosen et al. |
| 5,527,273 A | | 6/1996 | Manna et al. |
| 5,741,272 A | * | 4/1998 | Kuhne ........................ 606/128 |

FOREIGN PATENT DOCUMENTS

| | | | |
|---|---|---|---|
| DE | 3707567 | * 9/1987 | ................. 606/128 |
| DE | 37 07 921 A1 | 9/1987 | |
| DE | 37 20 424 A1 | 12/1987 | |
| EP | 0 437 851 A2 | 7/1991 | |
| JP | 62-224345 | 10/1987 | |
| WO | WO 87/01276 | 3/1987 | |
| WO | WO 92/02658 | 2/1992 | |
| WO | WO 94/12140 | 6/1994 | |
| WO | WO 96/38091 | 12/1996 | |

OTHER PUBLICATIONS

Richard Wolf Medical Instruments Corp, *Catalog*, pp. HA–D 91—HA–D 91a.
Richard Wolf Medical Instruments Corp, *Catalog*, p. D 61.
Karl Stroz, *Catalog*, p. URO–Geräte 4.

* cited by examiner

Primary Examiner—Glenn K. Dawson
(74) Attorney, Agent, or Firm—Welsh & Katz, Ltd.

(57) ABSTRACT

An improved rigid catheter is provided for lithotripsy. The catheter includes a rigid tube adapted to engage a lithotripsy transducer and power supply, with a restriction in an internal diameter of the rigid tube proximate a power delivery end of the rigid tube. The catheter may also include an enlargement on an external diameter of the tip. The tip may also be fabricated of a material considered to be very hard. The probe may also be solid with an enlarged tip.

8 Claims, 1 Drawing Sheet

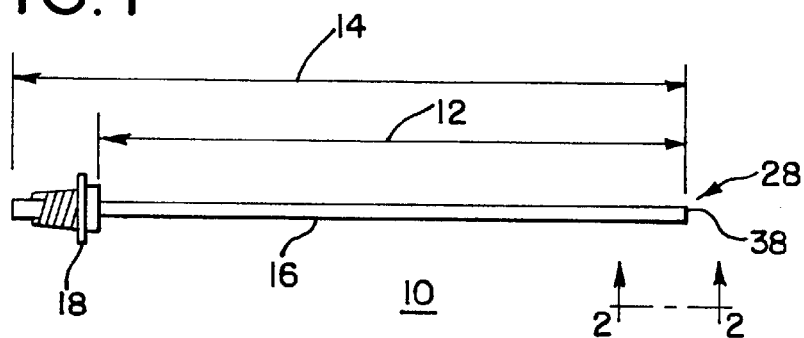
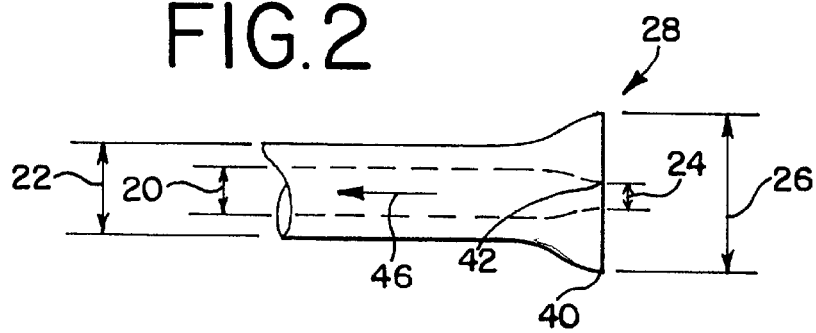
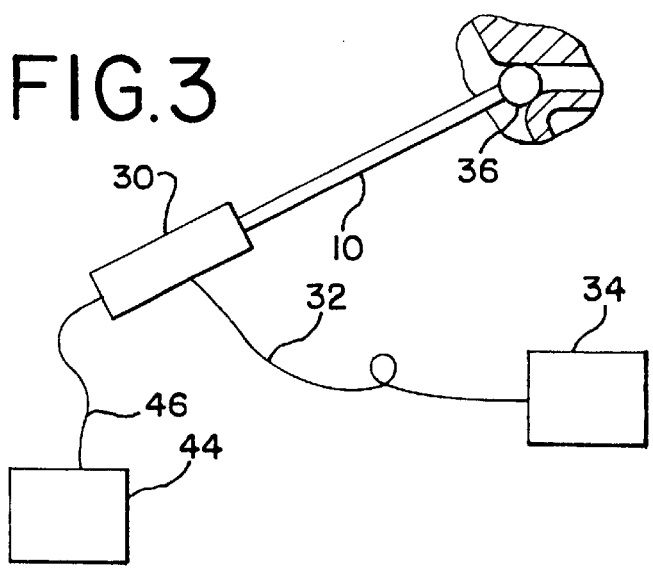

NON-CLOGGING CATHETER FOR LITHOTRITY

FIELD OF THE INVENTION

The field of the invention relates to lithotrity and more particularly to the probes used for crushing urethral calculi.

BACKGROUND OF THE INVENTION

Lithotrity (also commonly referred to as lithotripsy) is a well-known process for removing concretions, such as calculus stones, within human ducts such as the ureter or kidney. Under the process, a rigid probe is inserted into the body of the subject with a first end juxtaposed against the concretion. An ultrasonic signal is imposed onto the probe from a second end to break up the concretion.

The ultrasonic signal is typically generated by use of an electrically stimulated ultrasonic motor which may be rigidly attached to the probe. A variable power supply is used to supply a controlling signal to the ultrasonic motor.

The probe used is often hollow and typically made of an impervious material such as stainless steel. Often the tip used to contact and break up calculus stones is fabricated of a harder material.

The length of the probe is usually selected to be an integer multiple of one-half wavelength at the operating frequency. Selecting the probe to be an integer multiple of one-half wavelength at the operating frequency (and appropriate selection of tube thickness and coupling components) causes the probe to function as a resonator. The use of the probe as a resonator reduces the net power required to operate effectively.

An internal passageway of the probe is used to carry away debris generated by break-up of the concretion. The flow of fluid also functions to cool the probe during lithotripsy.

While lithotripsy using a rigid.probe.is effective, it is subject to a number of difficulties. As a concretion is broken-up, debris often accumulates and clogs the internal passageway of the probe. Clogging of the internal passageways of the probe often causes overheating of the probe, especially at higher power settings.

During break-up of the concretion, the probe will often bore a hole into the concretion and become lodged inside. Where relative movement between the probe and concretion ceases, break-up of the concretion effectively stops.

Accordingly, it is an object of the invention to restrict entry of debris into the passageway inside the probe until break-up of the concretion has progressed to a point where clogging is avoided.

It is a further object of the invention to provide a mechanism that prevents lodging of the probe tip within the concretion during break-up of the concretion.

SUMMARY

Briefly, these and other objects are provided by a rigid catheter for use in lithotripsy. The catheter includes a rigid tube adapted to engage a lithotripsy power supply and a restriction in an internal diameter of the rigid tube proximate a power delivery end of the rigid tube.

The catheter may also include an enlargement on an external diameter of the tip. The tip may also be fabricated of a material considered to be very hard.

DETAILED DESCRIPTION OF THE DRAWINGS

FIG. 1 depicts a side view of the catheter in accordance with an embodiment of the invention;

FIG. 2 depicts a partial side view of the tip of the catheter of FIG. 1;

FIG. 3 depicts an assembly view of a lithotriptor using the catheter of FIG. 1; and FIG. 4 depicts a cut-away side view of the tip of the catheter of FIG. 1 under an alternate embodiment.

DETAILED DESCRIPTION OF THE INVENTION

FIG. 1 is a side view of a rigid probe assembly (catheter) 10 which can be inserted into the body of a patient so as to operate on a caculi, stone or concretion 36 (FIG. 3), in accordance with an embodiment of the invention. The catheter 10 has a collar 18 at a first end which may be used to join the catheter to an ultrasonic motor 30 (FIG. 3).

Under the embodiment, the length of the probe 10 for a particular application may be approximately 14 inches. The tubing 16 may be #9 grade with an external diameter of 0.148 inches and an internal diameter of 0.117 inches. The length 12 of the tubing 16 and mass of the components (e.g., wall thickness, collar size, etc.) of the catheter assembly 10 are chosen so as to resonate at an operating frequency of the ultrasonic motor 30.

In addition to resonating at the operating frequency of the ultrasonic motor 30, the length 14 of the tubing 16 is also chosen as being an integer multiple of one-half wavelength at the operating frequency. Choosing the length 14 of the tubing 16 as being an integer multiple of one-half wavelength of the operating frequency ensures that the tip 28 of the catheter 10 will be at an ultrasonic anti-node of the resonant structure of the catheter 10. Placing the tip 28 at an ultrasonic anti-node results in a maximum vibration in that portion of the catheter 10 (i.e., the tip 28) which is in physical contact with the concretion 36.

The tubing 16 of the catheter 10 may be fabricated of a material appropriate for the environment of use (e.g., 301 stainless steel). The collar 18 may also be fabricated of stainless steel. The tubing 16 may be joined to the collar 18 by some appropriate technique (e.g., welding, brazing, etc.).

FIG. 2 depicts a portion of the tip 28 of the catheter 10. As shown, the tip 28 of the catheter 10 may be subject to a processing technique (e.g., swaging) appropriate to deform the tip 28 in such a way as to decrease the interior diameter 24. The probe 10 may also be processed to produce an enlargement 40 proximate the tip 28.

Swaging the tip 28 creates a restriction 42 of an appropriate reduced diameter 24 (e.g., a 17% reduction, or a final size of 0.100 inch for #9 tubing) inside the tip 28. The restriction 42 prevents debris from the concretion 36 from entering internal passageway 38 of the tube 16 until it has been reduced to a sufficiently small size to allow it to be aspirated through the tube 16 without plugging.

The enlargement 40 represents an increase 26 in the diameter of the tube 16 (e.g., a 3% increase in diameter to 0.152 inch for a #9 tube) proximate the tip 28. The enlargement 40 serves another important purpose. The enlargement 40 prevents the tip 28 of the probe 10 from entering and becoming lodged within the concretion 36 as it penetrates and breaks up the concretion 36.

During use (FIG. 3), the catheter 10 is inserted into the body of the patient and a tip 28 on a first, power delivery end of the catheter 10 is placed into contact with the concretion 36. An ultrasonic motor 30 is connected to a second end of the catheter 10 along with an aspiration tube 46 from an aspirator 44. A power supply 34 is connected to the ultrasonic motor 30 for purposes of driving the ultrasonic motor 34. The power supply 34 is adjusted to an appropriate frequency (e.g., 28 kHz) and power level and.lithotripsy is.allowed to begin.

As the catheter 10 begins to vibrate at an ultrasonic frequency under control of the ultrasonic motor 30 and power supply 34, power begins to be dissipated within the tubing 16 of the catheter 10. To cool the tubing 16, fluid 46 is aspirated through the restriction 42 along the channel 38 of the tubing 15, through the connecting handle 30 and tubing 46 and into an outflow collector within the aspirator 44.

Also as power is applied to the catheter 10, particles of the concretion 36 begin to abrade away due to an intimate contact and differential vibration between the tip 28 of the catheter 10 and the concretion 36. As the particles are abraded away they are drawn into and become entrained within the cooling fluid flowing through the passageway 38 of the catheter 10.

Alternatively, as power is applied to the catheter 10, the concretion 36 may break up, or large sections of the concretion 36 may break away from the concretion which are too large to pass through the passageway 38 without interfering with the walls of the passageway 38. The restriction 42 of the tip 28 of the catheter 10 prevents entry of the large sections of debris until the vibration of the tip 28 has reduced the debris to a size which will easily pass through the passageway 38 of the tubing 16 and aspiration device 44.

As the concretion 36 is abraded away, the tip 28 of the catheter 10 may progress into the concretion 36, effectively creating a hole in the concretion 36. The enlarged edge 40 of the tip 28 prevents lateral jamming of the tip 28 of the catheter 10 inside a hole of the concretion 36 and seizing between the tip 28 and concretion.

FIG. 4 is a cut-away view of a the tip 28 of the catheter 10 under another embodiment of the invention. Under the embodiment, the tip 28 is fabricated of a material (e.g., carbide, Nitronic 50, etc.) which may be much harder than the material of the tubing 16. The use of a harder tip material may provide enhanced durability over stainless steel or other more malleable materials.

As shown the tip 28 (FIG. 4) may be sleeved onto the tubing 16, through use of an interference fit. The tip 28 may also be joined to the tubing 16 by any other appropriate joining technology (e.g., brazing, welding, staking, etc.).

Specific embodiments of a novel apparatus for performing lithotripsy according to the present invention have been described for the purpose of illustrating the manner in which the invention is made and used. It should be understood that the implementation of other variations and modifications of the invention and its various aspects will be apparent to one skilled in the art, and that the invention is not limited by the specific embodiments described. Therefore, it is contemplated to cover the present invention any and all modifications, variations, or equivalents that fall within the true spirit and scope of the basic underlying principles disclosed and claimed herein.

What is claimed is:

1. A power delivery tip for a non-clogging catheter for engaging and pulverizing a calculi during lithotrity, such tip being disposed on a distal end of a tube forming a body of the catheter, such tube having a relatively constant inner and outer diameter defining a tube wall along a longitudinal axis of the tube, such tip comprising:

an enlarged annular flat surface transverse to the longitudinal axis of the tube for engaging the calculi on a power delivery end of the tip, such enlarged annular flat surface having an inner diameter of a smaller relative size than the inner diameter of the tube and an outer diameter of a larger relative size than the outer diameter of the tube; and a side wall of the tip coupling the tube wall and the annular flat surface and having a diverging wall thickness from the tube to the annular flat surface, said diverging wall thickness forming a relatively smooth transition in cross-section between a thickness of the tube wall and a thickness of the annulate of the annular flat surface of the power delivery end of the tip.

2. The power delivery tip for a non-clogging catheter as in claim 1 wherein the tip further comprises a swaged end on the rigid tube.

3. The power delivery tip for a non-clogging catheter as in claim 2 wherein the rigid tube and swaged end forming the tip further comprises stainless steel.

4. The power delivery tip for a non-clogging catheter as in claim 2 wherein the rigid tube and swaged end forming the tip further comprises a nickel-chromium alloy strengthened by additions of titanium and aluminum.

5. The power delivery tip for a non-clogging catheter as in claim 1 wherein the external diameter of the annular flat surface is approximately seventeen percent larger than the outer diameter of the rigid tube.

6. The power delivery tip for a non-clogging catheter as in claim 1 wherein the inner diameter of the annular flat surface is approximately three percent smaller than the inner diameter of the rigid tube.

7. The power delivery tip for a non-clogging catheter as in claim 1 wherein the tip further comprises an insert within the rigid tube.

8. The power delivery tip for a non-clogging catheter as in claim 7 wherein the insert forming the tip further comprises carbide.

* * * * *

UNITED STATES PATENT AND TRADEMARK OFFICE
CERTIFICATE OF CORRECTION

PATENT NO. : 6,582,440 B1
DATED : June 24, 2003
INVENTOR(S) : Brumbach

It is certified that error appears in the above-identified patent and that said Letters Patent is hereby corrected as shown below:

<u>Column 1,</u>
Line 37, the periods occurring before and after "probe" should be deleted.

<u>Column 2,</u>
Line 37, "301" should not be bolded.

<u>Column 3,</u>
Line 3, the period after the second "and" should be deleted.
Line 4, the period after the word "is" should be deleted.

<u>Column 4,</u>
Line 7, the word "for" should be -- on --. (first occurrence)
Lines 30 and 32, the word "rigid" should be deleted.
Lines 36-37, "strength-ened" should be deleted.
Line 40, "seventeen" should read -- three --.
Line 41, the word "rigid" should be deleted.
Line 44, the term "three" should read -- seventeen --.
Lines 45 and 48, the word "rigid" should be deleted.

Signed and Sealed this

Twenty-third Day of December, 2003

JAMES E. ROGAN
*Director of the United States Patent and Trademark Office*